US011337808B2

(12) United States Patent
McCarthy

(10) Patent No.: US 11,337,808 B2
(45) Date of Patent: May 24, 2022

(54) ANNULOPLASTY RING FOR RECEIVING A REPLACEMENT VALVE

(71) Applicant: Northwestern University, Evanston, IL (US)

(72) Inventor: Patrick M. McCarthy, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/735,128

(22) PCT Filed: Jun. 8, 2016

(86) PCT No.: PCT/US2016/036515
§ 371 (c)(1),
(2) Date: Dec. 8, 2017

(87) PCT Pub. No.: WO2016/200993
PCT Pub. Date: Dec. 15, 2016

(65) Prior Publication Data
US 2018/0168808 A1    Jun. 21, 2018

Related U.S. Application Data

(60) Provisional application No. 62/172,722, filed on Jun. 8, 2015, provisional application No. 62/241,664, filed on Oct. 14, 2015.

(51) Int. Cl.
*A61F 2/24* (2006.01)
(52) U.S. Cl.
CPC .......... *A61F 2/2445* (2013.01); *A61F 2/2418* (2013.01); *A61F 2/2448* (2013.01);
(Continued)

(58) Field of Classification Search
CPC ........ A61F 2/24; A61F 2/2445; A61F 2/2448; A61F 2/2418; A61F 2250/0029;
(Continued)

(56) References Cited

U.S. PATENT DOCUMENTS 4,489,446 A * 12/1984 Reed ...................... A61F 2/2448
137/846
4,917,698 A * 4/1990 Carpentier ............ A61F 2/2448
623/2.36
(Continued)

FOREIGN PATENT DOCUMENTS

FR    3004335 A1 * 10/2014   ............ A61F 2/2445

OTHER PUBLICATIONS

WIPO, U.S. International Search Authority, International Search Report and Written Opinion dated Sep. 9, 2016 in International Patent Application No. PCT/US2016/036515, 9 pages.
(Continued)

*Primary Examiner* — Seema Mathew
(74) *Attorney, Agent, or Firm* — Inskeep IP Group, Inc.

(57) ABSTRACT

An annuloplasty ring including elastic features that make the ring optimal for receiving a subsequent prosthetic valve via a "Valve In Ring Procedure." The elastic features provide a squeezing force on the native valve annulus that both ensures coaptation of the native valve leaflets and also prevents paravalvular leakage around a subsequently-placed prosthetic valve.

10 Claims, 7 Drawing Sheets

(52) U.S. Cl.
CPC ............ *A61F 2210/0014* (2013.01); *A61F 2230/0006* (2013.01); *A61F 2230/0019* (2013.01); *A61F 2230/0021* (2013.01); *A61F 2230/0091* (2013.01); *A61F 2230/0095* (2013.01); *A61F 2250/001* (2013.01); *A61F 2250/0018* (2013.01); *A61F 2250/0039* (2013.01)

(58) Field of Classification Search
CPC ........ A61F 2250/0039; A61F 2250/001; A61F 2/2466; A61F 2/2409; A61F 2/2427; A61F 2/2442; A61F 2230/0034; A61F 2/2454; A61F 2/2457
See application file for complete search history.

(56) References Cited

U.S. PATENT DOCUMENTS

| | | | |
|---|---|---|---|
| 6,102,945 A * | 8/2000 | Campbell | A61F 2/2448 623/2.36 |
| 6,217,610 B1 * | 4/2001 | Carpentier | A61F 2/2448 623/2.37 |
| 2001/0021874 A1 | 9/2001 | Carpentier et al. | |
| 2003/0040793 A1 | 2/2003 | Marquez | |
| 2005/0256569 A1 * | 11/2005 | Lim | A61F 2/2448 623/2.36 |
| 2007/0016287 A1 | 1/2007 | Cartledge et al. | |
| 2008/0086203 A1 | 4/2008 | Roberts | |
| 2010/0076549 A1 * | 3/2010 | Keidar | A61F 2/2445 623/2.36 |
| 2010/0152844 A1 | 6/2010 | Couetil | |
| 2010/0161047 A1 | 6/2010 | Cabiri | |
| 2012/0071970 A1 | 3/2012 | Carpentier et al. | |
| 2013/0331864 A1 | 12/2013 | Jelich et al. | |
| 2016/0310275 A1 * | 10/2016 | Jin | A61F 2/2448 |

OTHER PUBLICATIONS

Japanese Patent Office, Examination Report dated Aug. 21, 2020 in Japanese Patent Application No. 2017-564010, 5 pages.

* cited by examiner

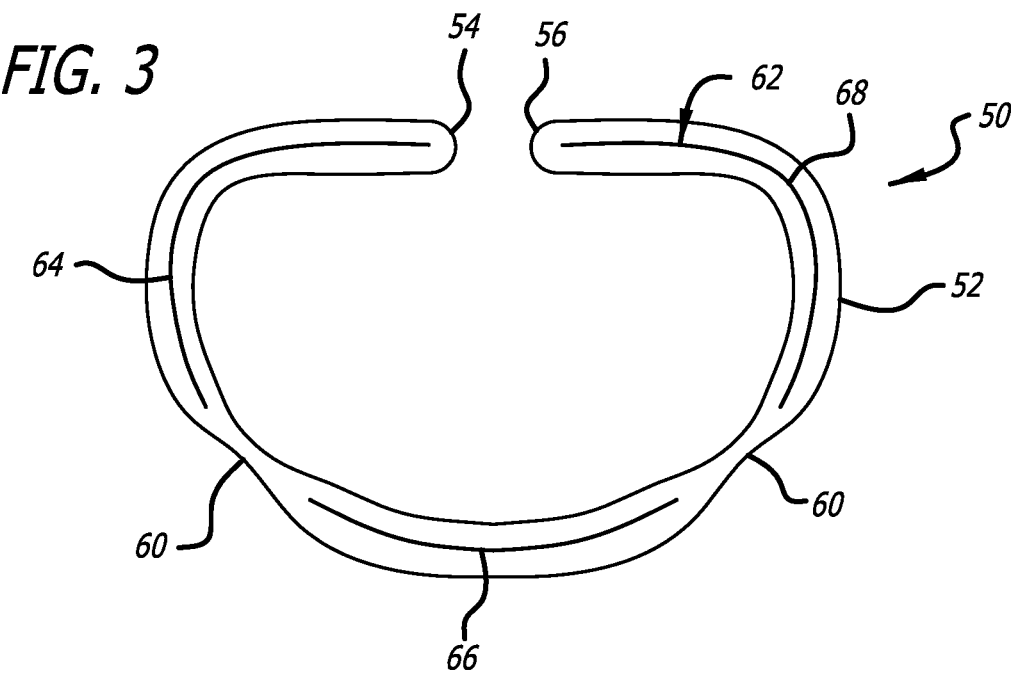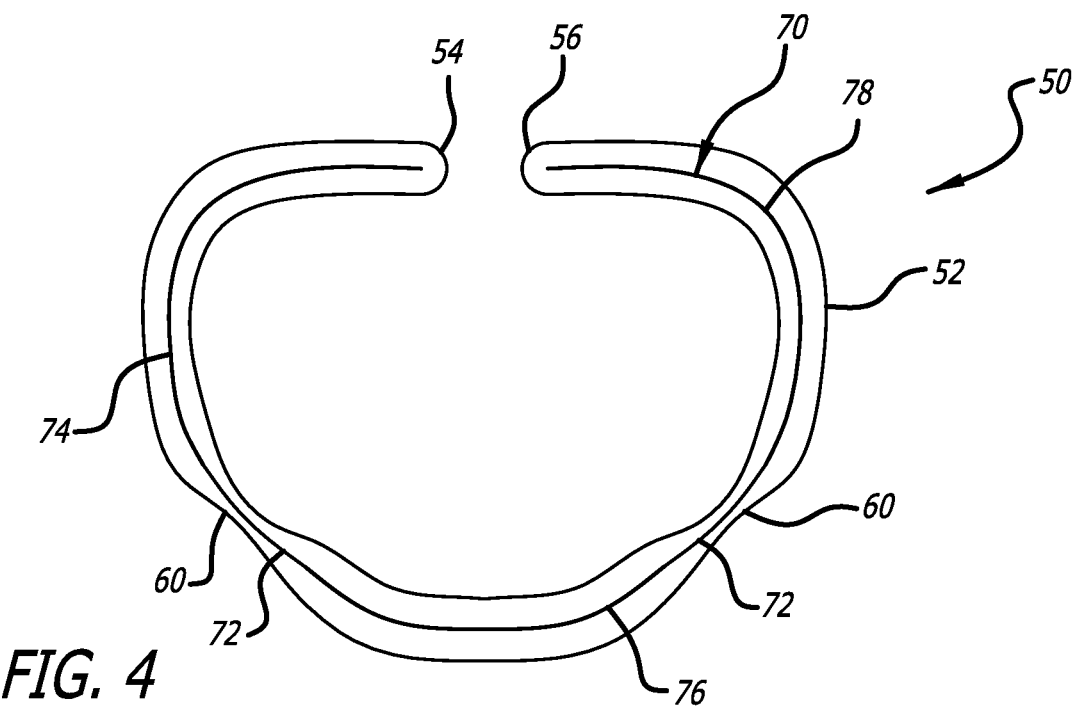

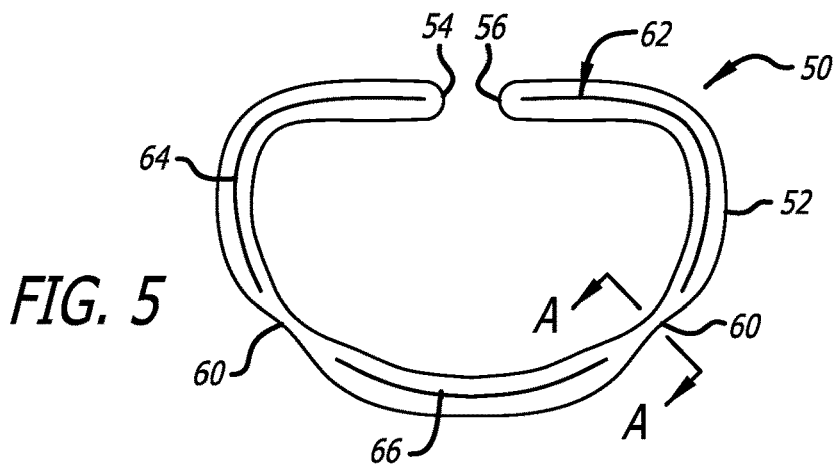
FIG. 5
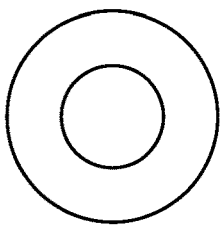 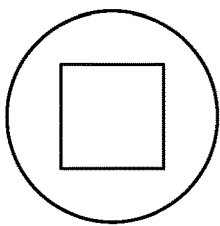 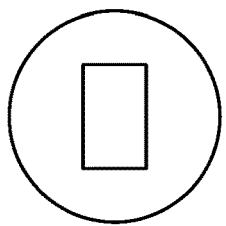 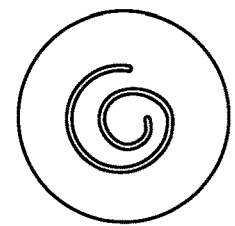
FIG. 5A  FIG. 5B  FIG. 5C  FIG. 5D
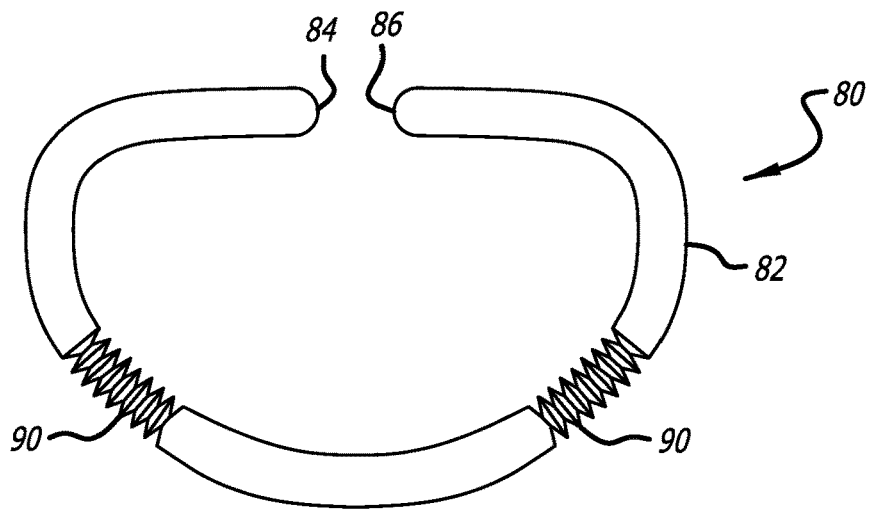
FIG. 6

*FIG. 7*
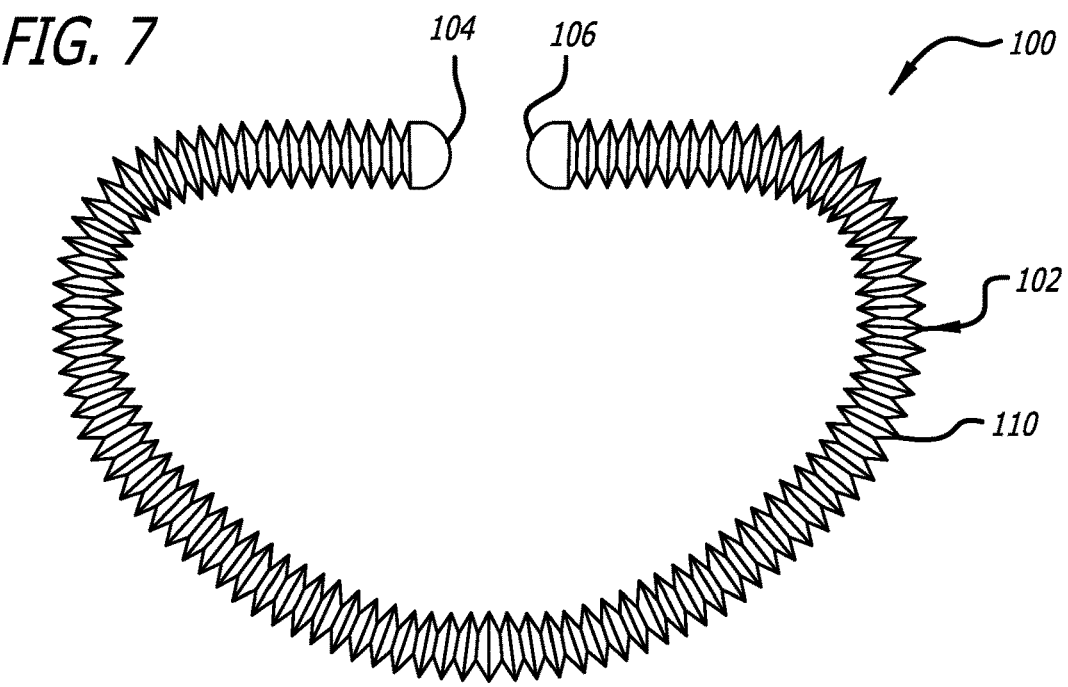
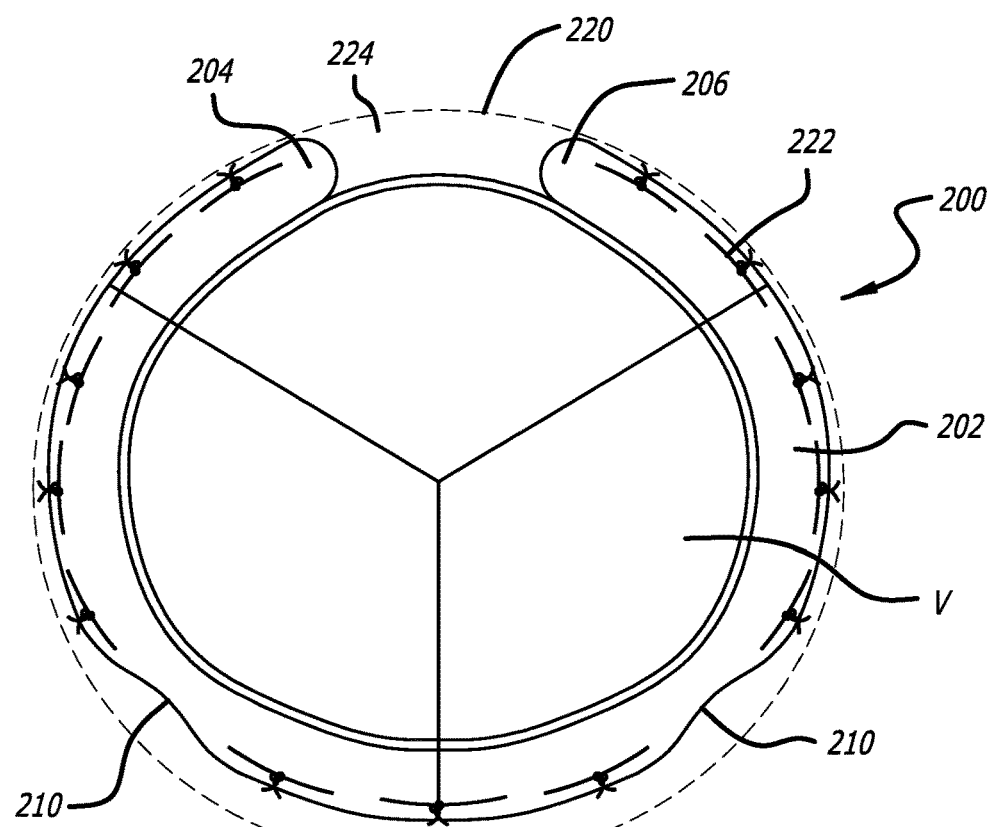
*FIG. 8*

ANNULOPLASTY RING FOR RECEIVING A REPLACEMENT VALVE

RELATED APPLICATIONS

This application is the U.S. National Phase of and claims priority to International Patent Application No. PCT/US2016/036515 filed Jun. 8, 2016 entitled Annuloplasty Rinq For Receiving A Replacement Valve, which claims benefit of and priority to U.S. Provisional Application Ser. No. 62/172,722 filed Jun. 8, 2015 entitled Annuloplasty Ring for Receiving a Replacement Valve, and U.S. Provisional Application Ser. No. 62/241,664 filed Oct. 14, 2015 entitled Annuloplasty Ring for Receiving a Replacement Valve, all of which are hereby incorporated herein by reference in their entireties.

FIELD OF THE INVENTION

The present invention relates to treatments for heart valve regurgitation, including mitral valve disease and tricuspid valve disease, and may be applicable for aortic and pulmonic valve disease.

BACKGROUND OF THE INVENTION

Annuloplasty rings and various methods of implanting such rings for the treatment of heart valve disorders has been known for several years, and represents a significant advancement in the treatment of heart disease. Annuloplasty rings are sutured, clipped, or otherwise secured to the patients valve annulus and are used to reduce the diameter of an enlarged or diseased heart valve, thereby allowing the valve leaflets to establish or reestablish coaptation, thereby reducing or eliminating regurgitant flow through the valve.

However, it has been observed in some patients that although the ring properly treats the diseased valve, the valve condition continues to worsen and thus necessitates a valve replacement. Historically such valve replacements have required another open heart surgery including first the excision of the annuloplasty ring followed by the implantation of a new valve. Although this multi-step process has proved useful and has saved and prolonged the lives of numerous patients, the excision and implantation process is time consuming and challenging for the operating physician, and potentially very dangerous for the patient. For example, if the condition of the valve and surrounding tissue is particularly diseased, the excision of the ring can often times render it very difficult to find suitable tissue to securely attach the new replacement valve.

The necessity of excising the ring at open heart surgery arises from the rigid, and/or non-resilient, non-conformable nature of existing rings. The ring also constricts the orifice of the valve and may not allow a properly sized prosthetic valve to be placed inside the ring. The ring also may distort the prosthetic valve causing a regurgitant leak within the prosthetic valve. The shape and size of the ring may not correspond well to the prosthetic valve and may lead to a regurgitant leak between the ring and the prosthetic valve called paravalvular regurgitation. Most rings are roughly D shaped and almost all prosthetic valve replacements are round so these spatial relationships have made the practical application of placing a valve inside a ring very difficult.

As a result, there is a distinct need for an annuloplasty ring that provides both an initial successful treatment of a diseased valve (e.g., treatment of valve regurgitation) and then provides, at a later date, a platform for receiving a replacement valve, should that patient's valve continue to deteriorate and require replacement. Such an annuloplasty ring would not require excision in such a circumstance, but, rather, would offer characteristics that enable placement and fixation of a prosthetic heart valve within the previously implanted annuloplasty ring.

SUMMARY OF THE INVENTION

The present invention is directed to meeting the aforementioned need for an annuloplasty ring that provides both an initial successful treatment of a diseased valve and a platform for receiving a replacement valve, sometimes referred to herein as a "Valve In Ring" or "VIR" procedure. The present invention accomplishes this by providing an annuloplasty ring that stretches and deforms around a prosthetic valve and then squeezes the prosthetic valve like a rubber band once released.

More specifically, the ring of the present invention that has an elongate core having a shape configured to establish an optimal perimeter for a human blood valve when implanted in a circulatory system and including at least one elastic feature allowing the core to be stretched from a resting state to a stretched state, and wherein the core is biased toward said resting state. The ring is implanted in a resting state designed to optimize performance of the patients own valve and the elastic nature of the ring also allows the ring to stretch in reaction to blood pressure forces and changes in blood flow. This allows the ring to more closely mimic native valve behavior as well as prevents undesired tissue stresses to be concentrated on areas surrounding ring fixation mechanisms such as sutures and the like. The stretching characteristic of the ring allows the ring to be stretched during valve in ring implantation such that it places a squeezing force on the native valve annulus that promotes long-term coaptation of the annulus to the prosthetic valve.

The squeezing characteristics of the elastic ring makes the ring stretchable and deformable, and therefore uniquely suited to receiving a prosthetic valve, such as an implanted transcatheter valve (TCV), a "sutureless valve" or other prosthesis. Due to the squeezing effect of the elastic, the ring functions as a gasket or rubber band around the prosthetic valve. The squeezing causes the ring to seal around the valve, thereby preventing paravalvular leakage.

One aspect of the invention provides an annuloplasty ring with a shape that is either a complete or incomplete circle or "D" shape which may also have a 3 dimensional appearance called a saddle shape. Circular shapes are typically used in association with anatomically circular valves, such as the aortic valve, whereas "D" shaped valves are typically used in association with anatomically "D" shaped or kidney-bean shaped valves such as the mitral valve. The tricuspid valve has a unique oblong variation of a saddle shape.

In another aspect of the invention, the elastic feature comprises at least one tapered section of the elongate core. The tapered section may have a cross-section that is shaped to provide optimal elastic performance characteristics. Non-limiting examples include circular, square, rectangular, and coil-shaped.

In yet another aspect of the invention, the at least one elastic feature takes the form of an accordion section, which may be short, relative to the length of the core, or may extend substantially the length of the core.

In still another aspect of the invention, the annuloplasty ring may include an inner wire extending through the elongate core. This inner wire may be included to increase the rigidity of the ring. Elasticity may be maintained by interrupting the inner wire in the areas of the at least one elastic feature. Alternatively, the inner wire may include areas of decreased diameter located in the locations of the at least one elastic feature.

The present invention also includes a method of treating or replacing a diseased heart valve. Initially, annuloplasty procedure is performed by installing an annuloplasty ring of the present invention around a regurgitant valve. The annuloplasty ring reestablishes coaptation of the native valve leaflets. If the native valve leaflets or surrounding structures become diseased later and it is determined that the diseased valve needs to be replaced, the method involves placing a prosthetic valve; using a transcatheter valve, sutureless valve, or through open heart surgery, within the installed annuloplasty ring. This is done without removing the ring and with or without removing the native heart valve. The prosthetic valve may be sewn or otherwise attached directly to the ring. The ring thus provides an ideally-shaped platform for receiving a prosthetic heart valve.

The present invention provides a ring that may be secured to the valve annulus via open surgery or percutaneously. Percutaneous approaches for implanting annuloplasty rings are currently under development. A percutaneous approach developed by Valtech Cardio of Or Yehuda, Israel, and called the Cardioband, provides an example and is incorporated by reference herein. More information is provided at http://www.valtechcardio.com. An embodiment of the device and method is shown and described in U.S. Pat. No. 8,715,342 to Zipory et al. and entitled, Annuloplasty Ring With Intra-Ring Anchoring, filed on May 7, 2009 and incorporated by reference herein. However, the Cardioband is not elastic and is not designed for receiving a prosthetic heart valve. The elastic nature of the ring, and especially the incomplete embodiments, make the ring especially suited for transcatheter delivery as well as accepting a subsequent prosthetic valve.

Another example, developed by Edwards Lifesciences Corp. of Irvine Calif. is described in U.S. Pat. No. 8,287,591 to Keidar et al. and entitled Transformable Annuloplasty Ring Configured to Receive a Percutaneous Prosthetic Heart Valve Implantation, filed on Sep. 19, 2008 and incorporated by reference herein. However, this device requires a balloon to expand the device in order to receive a prosthetic valve.

One skilled in the art will understand that the methods and ring embodiments of the present invention are novel and advantageous for several reasons, only a few of which include being designed for VIR procedures, providing optimal performance characteristics such as flexibility, deformability, radiopacity, and the obviation of pre-balloon procedures. Moreover the embodiments of the rings of the present invention, while being novel, provide a familiar appearance designed to optimize ease of use with a shallow learning curve for the implanting surgeon. The ring designs are also relatively easy to manufacture.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 3 is a plan view of an embodiment of a ring of the invention;

FIG. 4 is a plan view of an embodiment of a ring of the invention;

FIG. 5 is a plan view of an embodiment of a ring of the invention; FIGS. 5A-5D show various examples of cross-sectional shapes of elastic features of the ring, all of which are taken along section lines A-A of FIG. 5;

FIG. 6 is a plan view of an embodiment of a ring of the invention;

FIG. 7 is a plan view of an embodiment of a ring of the invention;

FIG. 8 is a plan view of an embodiment of a ring of the invention after a VIR procedure has been performed;

DESCRIPTION OF THE EMBODIMENTS OF THE INVENTION

Figure 1:
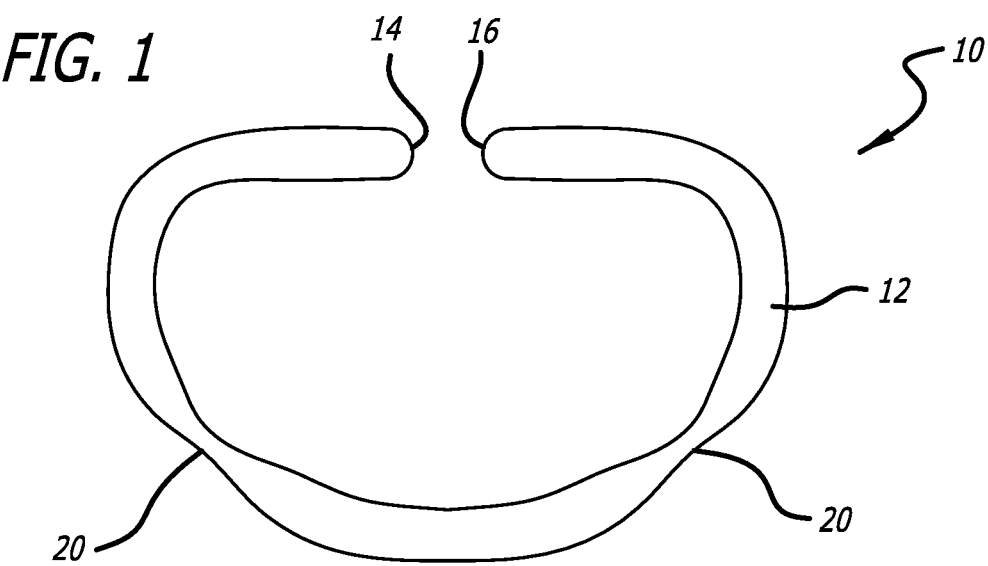
FIG. 1 is a plan view of an embodiment of a ring of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Referring now to the figures, and first to FIG. 1, there is shown an embodiment 10 of an annuloplasty ring of the invention. The ring 10 generally includes an elongate core 12 that extends between a first end 14 and a second end 16. Though shown only in FIG. 8, all of the ring embodiments described herein may be covered with a material as is common in the art by, for example, a double velour fabric or other Dacron fabric. Such a fabric assists in anchoring by providing a medium for receiving sutures and also promoting in-growth of tissue. Additionally, depending on the performance of the selected core material, the need for a cover may be obviated.

The core 12 has a shape configured to establish an optimal perimeter for a human blood valve when implanted in a circulatory system. For example, the ring 10 shown in FIG. 1 has a "D" shape, and a 3 dimensional saddle shape, that corresponds to the mitral valve of the heart.

All of the various ring embodiments described herein include an elastic feature that give the ring an elastic stretchability from a resting state to a stretched state. Like a rubber band, the ring is implanted in its resting state, but is flexible and allows for normal stretching and function of the valve. When the ring is in the stretched state, a squeezing force is imparted on the object or forces, such as blood pressure, that are placing the device in the stretched state. The squeezing characteristics of the elastic ring makes the ring both stretchable and deformable, and therefore uniquely suited to receiving a prosthetic valve, such as an implanted transcatheter valve (TCV) or other prosthesis. Due to the squeezing effect of the elastic, the ring and the annular tissue to which it is fixed function as a gasket or rubber band around the prosthetic valve. The squeezing causes the ring and tissue to seal around the valve, thereby preventing paravalvular leakage and reducing the risk that the valve may move, migrate, or embolize.

More specific to the embodiment shown in FIG. 1, the ring 10 includes at least one elastic feature 20 that allows the core to be stretched from a resting state to a stretched state. In this embodiment 10, the elastic feature 20 takes the form of a tapered section having a cross-section that is smaller than a cross-section of the rest of the core 12.

Figure 2:
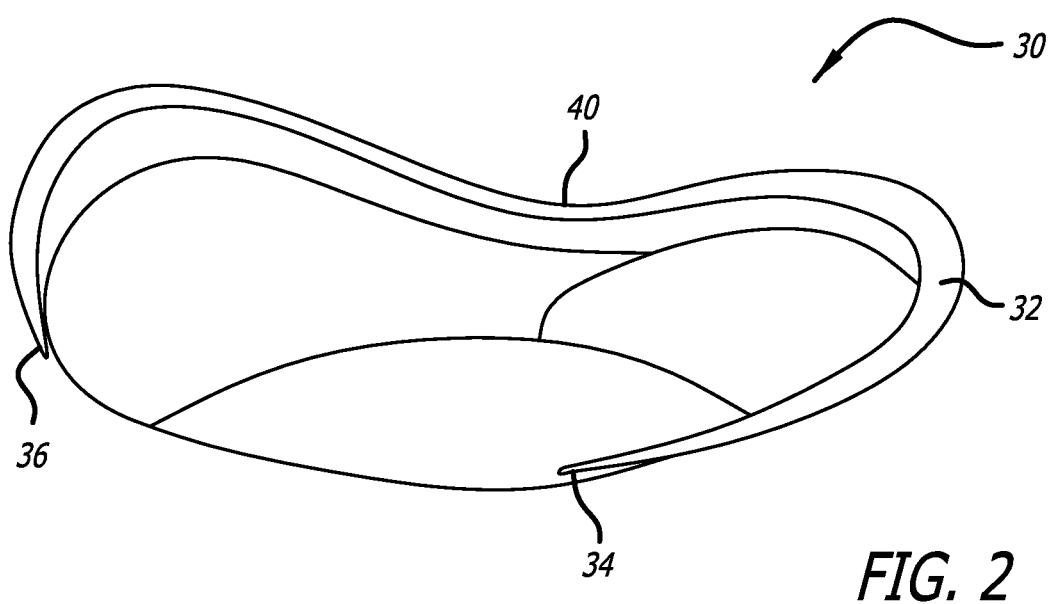
FIG. 2 is a perspective view of an embodiment of a ring of the invention having been placed at a target valve site.

By way of example, the ring 10 shown in FIG. 1 has two tapered sections 20. The number and placement of the tapered sections 20 may vary according to the intended implantation location and orientation of the ring 10. For example, FIG. 2 shows an embodiment 30 of a ring having an oblong shape to conform to the tricuspid valve. A round native valve such as the aortic valve or pulmonary valve also may be treated with a ring. The ring 30 has a core 32 that extends between ends 34 and 36 and includes a single tapered section 40 between the ends 34 and 36. The tapered section 40 is aligned with a commissure of the tricuspid valve. Ends 34 and 36 are also shown as being tapered.

One skilled in the art will understand that an annuloplasty ring is sized to accommodate a native valve but, once attached, given the elastic nature of the tissue, also imparts a force on the tissue. Thus, when it is written herein that the valve is sized and shaped to conform to a native valve, it is to be understood that the native valve annulus will, to an extent, also conform to the ring. The latter conformation is necessary to reestablish coaptation of the leaflets. Therefore, the ring is not shaped to precisely conform to a diseased valve. Rather, the ring is sized and shaped to reshape the native valve annulus to a desired configuration once implanted.

In order to impart the desired forces on the target tissue, the elongate core of the various embodiments described herein is flexible and resilient. The core may be constructed of an appropriate, biocompatible material such as silicone, medical-grade rubber, e ptfe, Goretex® or others. Alternatively, other materials may be used that are covered with a silicone layer. In some cases, additional rigidity may be desired beyond the capabilities of the selected core material. Additional rigidity may be provided by utilizing a wire core. For example, FIG. 3 shows an embodiment 50 of a ring having a core 52 that extends in a "D" shape between a first end 54 and a second end 56 and includes two tapered sections 60. An inner wire 62 extends through the core 52 to add rigidity. The inner wire 62 may be constructed of biocompatible materials including, but not limited to, Nitinol or an alloy, stainless steel, cobalt chromium, titanium, nickel or others. As seen in FIG. 3, the inner wire 62 is configured to not interfere with the elasticity provided by the tapered sections 60. The inner wire 62 is interrupted to form three sections of wire, 64, 66, and 68. The three sections 64, 66 and 68 are interrupted, or spaced apart, at the tapered sections 60.

Alternatively, if more rigidity is required at the tapered sections, an embodiment 70 of an inner wire, such as that shown in FIG. 4, may be provided. FIG. 4 shows a ring 50, such as that shown in FIG. 3, wherein the interrupted inner wire 62 has been replaced with a non-interrupted inner wire 70. The inner wire 70, however, has areas 72 of reduced diameter corresponding to the tapered sections 60. The areas 72 of reduced diameter result in the formation of three sections 74, 76, and 78 of relatively increased diameter. These sections 74, 76 and 78 are thus located in the more robust areas of the core 52 between the tapered sections 60.

The inner wire 62 may also add radiopacity to the ring. If additional radiopacity is desired, marker bands or coating may also be incorporated in the silicone or fabric.

In addition to the use or non-use of inner wires, the elastic characteristics of the tapered sections may be controlled by the use of various cross-sectional shapes at the tapered sections. For example, FIG. 5 shows the ring 50 of FIG. 3 as described above. Various cross-sectional shapes are also shown, taken along section lines A-A, which extend through the tapered section 60. FIG. 5A shows a circular cross-section; FIG. 5B shows a square cross-section; FIG. 5C shows a rectangular cross-section; and FIG. 5D shows a spiral or coil-shaped cross section. Each shape will exhibit different flexibility and stretching characteristics and the examples provided should be viewed as non-limiting.

The elastic characteristics of the ring may further be varied by employing other embodiments of the elastic features. For example, referring now to FIG. 6, there is shown an embodiment 80 of a ring of the invention. The ring 80 generally includes an elongate core 82 that extends between a first end 84 and a second end 86. The core 82 has a "D" shape that corresponds to the mitral valve of the heart but may also be shaped to conform to other valves, such as oblong valves like the tricuspid valve, or to circular valves.

The ring 80 includes at least one elastic feature 90 that allows the core to be stretched from a resting state to a stretched state. In this embodiment 80, the at least one elastic feature 90 takes on the form of an accordion section 90 in an otherwise-cylindrical core 82. The at least one accordion section 90 of FIG. 6 is shown by way of example as two spaced apart accordion sections 90, that may or may not be placed to coincide with the commissures of the target heart valve.

Alternatively, to provide different elastic characteristics, there is provided an embodiment 100, shown in FIG. 7, that generally includes an elongate core 102 that extends between a first end 104 and a second end 106. The core 102 has a "D" shape that corresponds to the mitral valve of the heart but may also be shaped to conform to other valves, such as circular valves or oblong like the tricuspid valve.

The ring 100 includes an elastic feature 110 that allows the core to be stretched from a resting state to a stretched state. In this embodiment 100, the at least one elastic feature 110 takes on the form of an accordion section 110 that extends substantially along the entire extent between the first end 104 and the second end 106. It is understood that the various features shown in the embodiments herein may be employed by other embodiments, even if all the variations are not shown in the figures. For example, the embodiments incorporating accordion-like elastic features may be used in conjunction with inner wires if increased rigidity is desired.

Further variation of performance characteristics may be provided by embodiments of the invention that comprise complete rings. Heretofore, the embodiments described have all constituted incomplete rings, including first ends and second ends with elongate cores that extend between the two ends. It should be noted that these incomplete cores may be used in conjunction with cloth covers that are either incomplete, to match the cores, or complete, thereby spanning the gap between the first end and the second end of the core with cloth. In this case, it may be desirable to suture only the areas of the ring including a core. An embodiment of this can be seen in FIG. 8 which shows an embodiment 200 of a round, incomplete ring, having an elongate core 202 extending between a first end 204 and a second end 206. The core 202 includes at least one elastic feature 210 in the form of a taper. The ring 200 also includes a cloth cover 220, shown in phantom lines to reveal the detail of the core 202. Sutures 222 are used to secure the ring 200 to the valve annulus, and a prosthetic valve V has been placed in the ring 200 via a VIR procedure. The sutures 222 extend through the cloth 220 and the core 202 but are not included in the gap 224 between the first end 204 and the second end 206.

Figure 9:
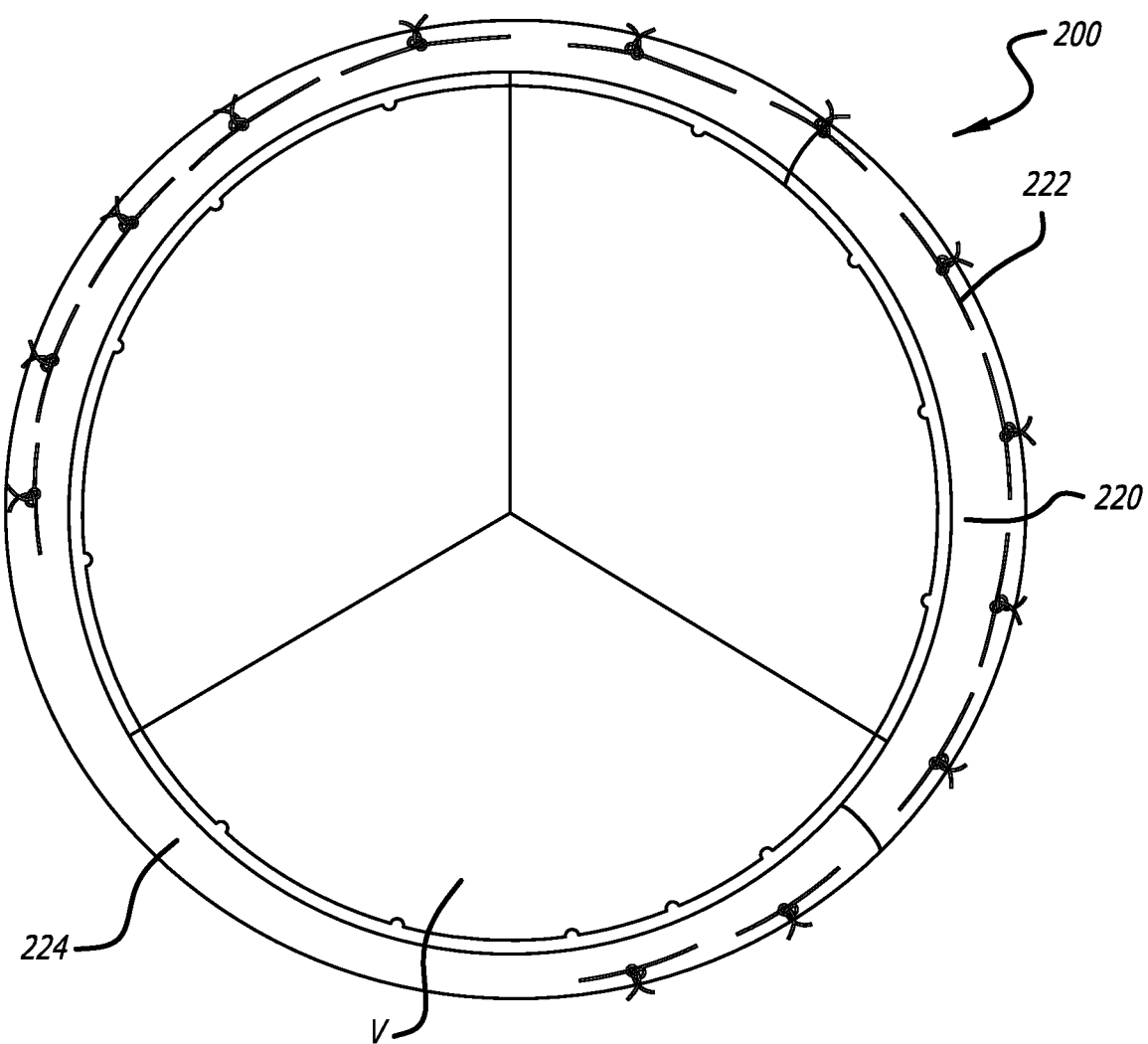
FIG. 9 is a plan view of an embodiment of a ring of the invention having a cover and after a VIR procedure has been performed.
Figure 10:
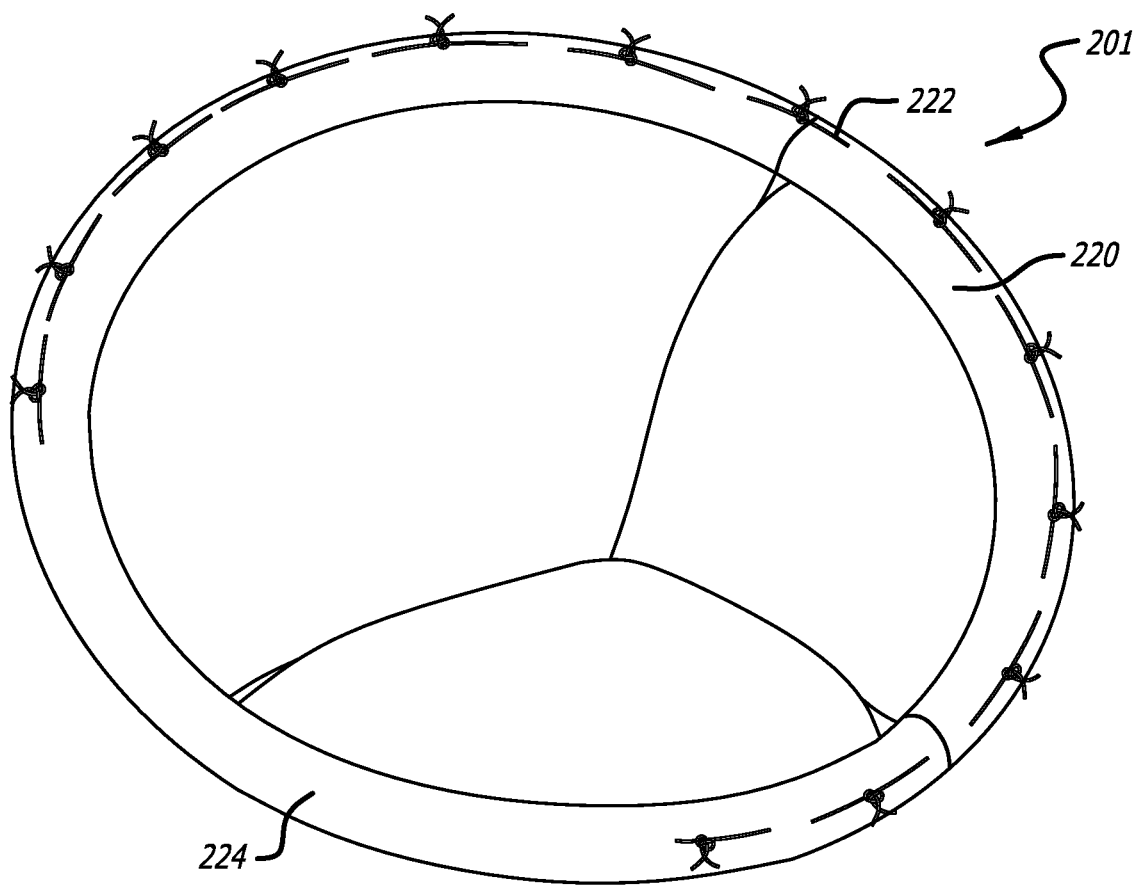
FIG. 10 is a perspective view of embodiment of a ring of the invention implanted in the annulus of a tricuspid valve.

FIG. 9 shows the embodiment 200 of FIG. 8 with the cloth cover 220 covering the core (not shown). The ring 200 has a valve V implanted therein. The sutures 222 extend around the perimeter of the ring 200 except in the gap area 224 where the core of the ring 220 is incomplete. The embodiment of FIG. 9 is round, like an aortic valve. FIG. 10 shows a similar embodiment 201, including a cloth cover 220, sutures 222 and a gap area 224. Embodiment 201 differs from 200 only in that it has an oblong shape suited for a tricuspid valve. Embodiment of 201 is shown as implanted in the annulus of a tricuspid valve. A prosthetic valve has not been implanted in the ring 201, but can be if necessary in the future.

Figure 11:
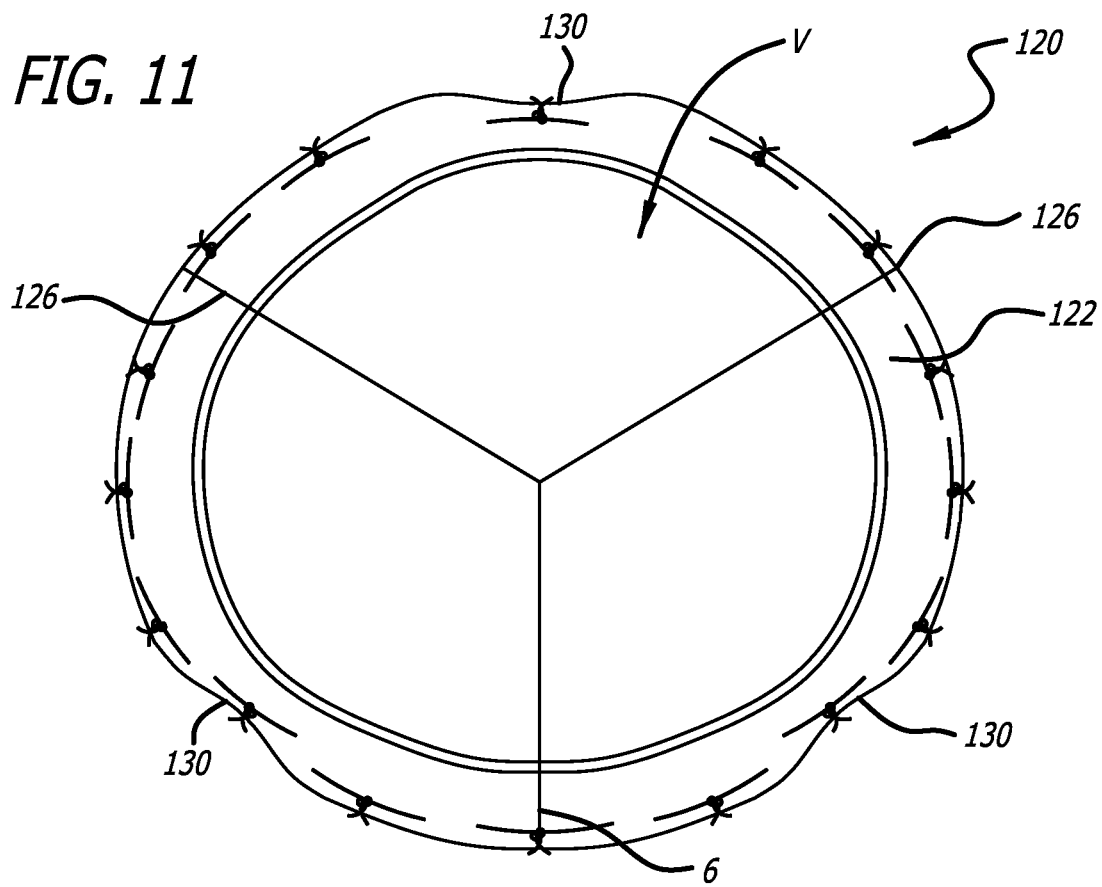
FIG. 11 is a plan view of an embodiment of a ring of the invention after a VIR procedure has been performed; and, FIG. 12 is a plan view of an embodiment of a ring of the invention.

Referring now to FIG. 11, there is shown an embodiment 120 of a ring having a complete shape that generally forms a circle to correspond to a valve such as the mitral valve. Elastic features 130 are shown as tapered sections, as described above. Because the ring 120 is complete, three tapered sections 130 are optionally provided to give uniform elastic traits. The elastic features 130 are placed in FIG. 8 in the middles of the leaflets, rather than at the commissure points, as shown in some of the aforementioned embodiments. The ring 120 optionally includes markers 126 such that the elastic features 130 of the ring 120 are easily visualized and correctly placed.

FIG. 11 is also shown as including a prosthetic valve V installed within the ring 120. It is to be understood that all of the embodiments of rings described herein are designed to provide optimal attachment platforms for prosthetic valves, even after the rings have been implanted and in use in situ for long periods of time, if necessary. Furthermore, the embodiment 120 shown in FIG. 11 is shown, by way of example, as having been sutured in place in a patient. It is thought that the complete ring of FIG. 11, may be better suited for surgical implant instead of percutaneous implant.

Figure 12:
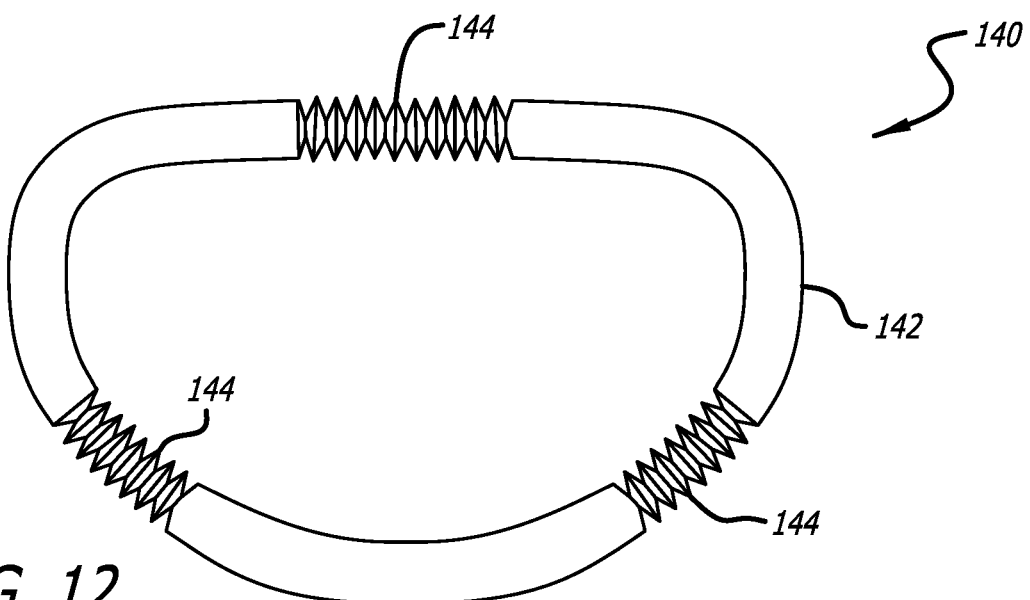

The embodiment 140 of FIG. 12 demonstrates a complete ring 140 in the shape of a "D". The ring 140 has a core 142 and one or more elastic features 144 that comprise accordion sections, in this case three accordion sections, spaced apart around the circumference of the ring 140. The number of and lengths of the accordion sections may vary, as described above. The entire D ring may be a continuous accordion section.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An annuloplasty ring for receiving a replacement prosthetic valve comprising:
    a closed elongate core having a shape configured to establish a preferred perimeter for a human blood valve when implanted in a circulatory system, wherein the core comprises an elastic material such that said core is movable from a resting state to a stretched state by said replacement prosthetic valve during a replacement valve procedure, wherein said stretched state of said core has a perimeter that is larger than the preferred perimeter;
    a plurality of rigid members embedded in said core with spaces therebetween, said spaces concentrating elastic properties of the core into areas of increased stretchability, the areas of increased stretchability placed to align with commissures of the human blood valve;
    said plurality of rigid members adding rigidity to said core in both said resting state of said core and said stretched shape of said core; and,
    a cover, covering the core;
    and wherein said core is biased toward said resting state, such that when said replacement prosthetic valve is implanted within said ring, said areas of increased stretchability ensure placement of a squeezing force of said core on the replacement prosthetic valve to prevent paravalvular leakage.

2. The annuloplasty ring of claim 1 wherein said shape comprises an incomplete circle.

3. The annuloplasty ring of claim 1 wherein said shape comprises a complete circle.

4. The annuloplasty ring of claim 1 wherein said shape comprises an incomplete "D" shape that mimics a healthy mitral valve perimeter.

5. The annuloplasty ring of claim 1 wherein said shape comprises an incomplete "D" shape that mimics a healthy mitral valve perimeter.

6. The annuloplasty ring of claim 1 wherein each of said spaces creates a tapered section of said elongate core.

7. The annuloplasty ring of claim 6 wherein said plurality of rigid members comprises a cross section selected from the group including: circular, square, rectangular, coil-shaped.

8. The annuloplasty ring of claim 1 wherein said plurality of rigid members comprises a plurality of wires.

9. The annuloplasty ring of claim 1 wherein said plurality of rigid members comprises three rigid members.

10. The annuloplasty ring of claim 1 wherein a number of said spaces corresponds to a number of leaflets of a valve into which said ring is to be placed.

\* \* \* \* \*